United States Patent [19]

Becker et al.

[11] Patent Number: 5,196,547
[45] Date of Patent: Mar. 23, 1993

[54] MESO-AZACYCLIC AMIDES OF IMIDAZOPYRIDINE CARBOXYLIC ACIDS AND ANALOGS THEREOF

[75] Inventors: Daniel P. Becker, Glenview; Daniel L. Flynn, Mundelein; Alan E. Moormann, Skokie; Roger Nosal, Buffalo Grove; Clara I. Villamil, Glenview, all of Ill.

[73] Assignee: G. D. Searle & Co., Chicago, Ill.

[21] Appl. No.: 896,293

[22] Filed: Jun. 10, 1992

Related U.S. Application Data

[62] Division of Ser. No. 666,278, Mar. 7, 1991, Pat. No. 5,137,893.

[51] Int. Cl.$^5$ .................. C07D 487/04; A61K 31/40
[52] U.S. Cl. .................................................. 548/453
[58] Field of Search .......................... 548/453; 514/413

[56] References Cited

U.S. PATENT DOCUMENTS

| | | | |
|---|---|---|---|
| 4,273,778 | 6/1981 | Hadley et al. | 424/265 |
| 4,336,259 | 6/1982 | Hadley et al. | 424/265 |
| 4,472,413 | 9/1984 | Hadley et al. | 424/267 |
| 4,605,662 | 8/1986 | Miyano et al. | 548/453 |
| 4,751,231 | 6/1988 | Halczenko et al. | 548/453 |
| 4,797,387 | 1/1989 | King | 514/212 |
| 4,797,406 | 1/1989 | Richardson et al. | 514/299 |
| 4,816,453 | 3/1989 | Watts | 514/217 |

FOREIGN PATENT DOCUMENTS

| | | |
|---|---|---|
| 67121/87 | 7/1987 | Australia. |
| 0083694 | 5/1983 | European Pat. Off. ............ 548/453 |
| 093488 | 11/1983 | European Pat. Off.. |
| 0189002 | 7/1986 | European Pat. Off.. |
| 0201165 | 11/1986 | European Pat. Off.. |
| 0220011 | 4/1987 | European Pat. Off.. |
| 0230718 | 6/1987 | European Pat. Off.. |
| 0315390 | 5/1989 | European Pat. Off.. |
| 0323077 | 7/1989 | European Pat. Off.. |
| 2152049 | 7/1985 | United Kingdom. |
| 2166726 | 5/1986 | United Kingdom. |
| 2169292 | 7/1986 | United Kingdom. |

OTHER PUBLICATIONS

Fludzinski et al., J. Med. Chem., Inazoles as Indole Bioesters, 30 No. 9, 1535–7, Apr. 19, 1987.

Primary Examiner—David B. Springer
Attorney, Agent, or Firm—Cynthia S. Kovacevic; Paul D. Matukaitis; Roger A. Williams

[57] ABSTRACT

The imidazopyridines containing meso-azacycle side chains as described herein find utility as antagonists of the serotonin 5-HT$_3$ receptor. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbancies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

6 Claims, No Drawings

MESO-AZACYCLIC AMIDES OF IMIDAZOPYRIDINE CARBOXYLIC ACIDS AND ANALOGS THEREOF

This is a division of application Ser. No. 07/666,278, filed Mar. 7, 1991, U.S. Pat. No. 5,137,893.

BACKGROUND OF THE INVENTION

The invention herein is directed to compounds and a method of treating gastrointestinal motility disorders of a mammal by administering to the mammal in need thereof a therapeutically effective amount of a compound disclosed herein or a pharmaceutically acceptable salt thereof. The method can be practiced to treat gastrointestinal motility disorders such as gastroesophageal reflux, diseases characterized by delayed gastric emptying, ileus, irritable bowel syndrome, and the like. The compounds of the invention are serotonergic 5-HT$_3$ antagonists and as such are useful for the treatment of conditions, for example, such as anxiety, psychoses and depression.

There are classes of compounds known for the treatment of such disorders. For example, azatetracycle compounds are disclosed in co-pending U.S. patent application Ser. No. 07/515,391 filed Apr. 27, 1990, and N-Azabicyclo [3.3.0] octane amides of aromatic acids are disclosed in co-pending application Ser. No. 07/406,205 filed Sept. 11, 1989.

Aza-adamantyl compounds are disclosed in U.S. Pat. No. 4,816,453 and are mentioned generically in U.K. Patent 2,152,049A and European application 0189002A2.

Azabicyclic nonanes are disclosed in European Patent application 0094742A2. Additional azabicyclic compounds are disclosed in U.S. Pat. Nos. 4,797,387 and 4,797,406.

Benzamides have been known as 5-HT$_3$ antagonists and as compounds possessing gastrointestinal motility-enhancing properties. Benzamides of the following formula:

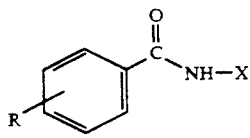

compounds wherein X can be an azabicycloalkane moiety and which exhibit gastrointestinal motility enhancing and/or 5-HT$_3$ antagonist properties are disclosed in EP 0094742A2 and in U.S. Pat. No. 4,797,406. In addition, UK Patent 2,152,049 discloses that certain benzamide derivatives exhibit serotonin M antagonistic activity.

Indoleamides of the following formula have also been described as possessing gastrointestinal motility-enhancing and/or 5-HT$_3$ antagonist properties:

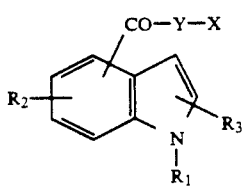

Compounds wherein X contains an aminergic side chain or an azabicycloalkane moiety are described in U.S. Pat. No. 4,797,406.

European patent publication number 0,230,718 discloses certain substituted benzamide derivatives, substituted with piperidinyl analogues as having gastrointestinal motility-enhancing and/or antiemetic activity and/or 5-HT receptor antagonist activity.

J. Heterocyclic Chemistry (1987) 24: 47 describes the preparation of the following compound: No substitution is shown in the phenyl ring and no utility is described.

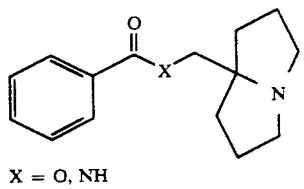

X = O, NH

J. Pharmaceutical Sciences (1987) 76: 416 describes compounds of generic scope. Utility as anti-arraythmic agents is described.

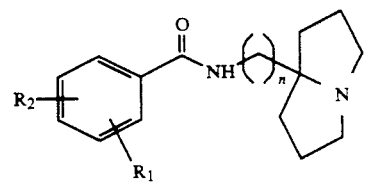

n=1 or 2
R$_1$=H, 2-Me, 4-NH$_2$, 4-OMe, 4-NHCO$_2$Et, 2-OEt, 4-OEt, 3- or 4-NMe$_2$3- or 4-NO$_2$; R$_2$=H or 6-Me.

JP Patent 58083694 A2 and JP 0027355B describe antiarrythmic agents of the following formula wherein n=1 or 2; R$_1$ or R$_2$ are both Me or R$_1$ is H while R$_2$ is nitro, dilower alkylamino, lower alkoxycarbonylamini, or athoxy.

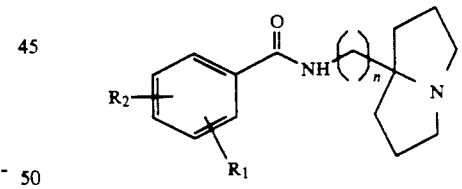

EP Patent 39,903 and U.S. Pat. No. 4,617,401 describe compounds of the following formula wherein X is NH or O and R is H, OMe, OH, or NH$_2$ and Z is a lone electron pair of optionally substituted alkyl group. The compounds are described as spasmolytic, antiarrythmic, and neuromuscular-blocking agents.

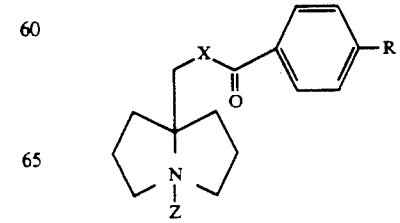

SUMMARY OF THE INVENTION

The compounds of examples 1-8 find utility as antagonists of the serotonin 5-HT$_3$ receptor. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbancies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

DETAILED DESCRIPTION OF THE INVENTION

The invention herein is directed to compounds of the formula

Ar—CO—X—Z the stereoisomers and pharmaceutically acceptable salts thereof wherein Ar represents a radical of the formula.

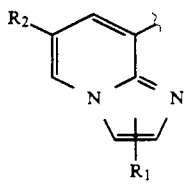

A

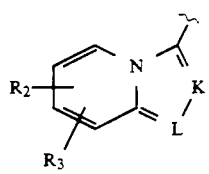

B

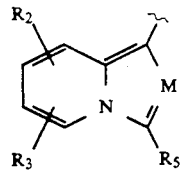

C

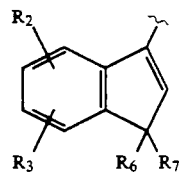

D

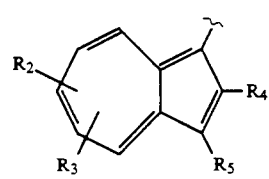

E

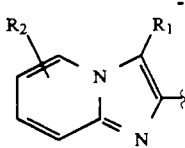

F

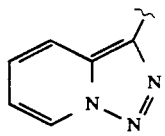

G

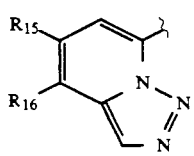

H

Wherein
in-Group A, R is H, or C$_{1-6}$ alkyl, R$_2$ is H, or halogen;

In Group B, K is N or CR$_4$, L is N or CR$_5$, R$_2$ and R$_3$ are independently H or halogen, R$_4$ is H, or C$_{1-6}$ alkoxy, R$_5$ is H, halogen, CF$_3$, C$_{1-6}$ alkyl, C$_{1-6}$ alkoxy, C$_{1-6}$alkylthio, C$_{1-6}$ alkylsulfonyl, C$_{1-6}$ alkylsulfinyl, C$_{1-7}$ acyl, cyano, C$_{1-6}$ alkoxycarbonyl, C$_{1-7}$ acylamino, hydroxy, nitro, amino, aminocarbonyl, or aminosulfonyl optionally N-substituted by one or two groups selected from C$_{1-6}$ alkyl, C$_{3-8}$ cycloalkyl, and C$_{3-8}$ cycloalkylC$_{1-4}$alkyl or disubstituted by C$_4$ or C$_5$ polymethylene, phenyl or phenyl C$_{1-4}$ alkyl group optionally substituted in the phenyl ring by one or two of halogen, C$_{1-6}$ alkoxy or C$_{1-6}$ alkyl groups;

In Group C, M is N or CR$_4$, R$_2$ and R$_3$ are independently H or halogen, R$_4$ is H or C$_{1-6}$ alkoxy, R$_5$ is H, halogen, CF$_3$, C$_{1-6}$ alkyl, C$_{1-6}$ alkoxy, C$_{1-6}$alkylthio, C$_{1-6}$ alkylsulfonyl, C$_{1-6}$ alkylsulfinyl, C$_{1-7}$ acyl, cyano, C$_{1-6}$ alkoxycarbonyl, C$_{1-7}$ acylamino, hydroxy, nitro, amino, aminocarbonyl, or aminosulfonyl optionally N-substituted by one or two groups selected from C$_{1-6}$ alkyl, C$_{3-8}$ cycloalkyl, and C$_{3-8}$ cycloalkylC$_{1-4}$alkyl or disubstituted by C$_4$ or C$_5$ polymethylene, phenyl or phenyl C$_{1-4}$ alkyl group optionally substituted in the phenyl ring by one or two of halogen, C$_{1-6}$ alkoxy or C$_{1-6}$ alkyl groups;

In Group D, one of R$_6$ or R$_7$ is C$_{1-6}$ alkyl and the other is C$_{1-6}$ alkyl, phenyl or phenyl C$_{1-4}$ alkyl optionally substituted in either phenyl ring by one or two of C$_{1-6}$ alkyl, C$_{1-6}$ alkoxy, or halogen, or R$_6$ and R$_7$ together are C$_{2-6}$ polymethylene or C$_{2-5}$ polymethylene interrupted by an —)— linkage, linkage, R$_2$ and R$_3$ are independently H or halogen;

In Group E, R$_4$ is H or C$_{1-6}$ alkoxy, R$_5$ is H or C$_{1-6}$ alkoxy, R$_2$ is H, halogen, CF$_3$, C$_{1-6}$ alkyl, C$_{1-6}$ alkoxy, C$_{1-6}$alkylthio, C$_{1-6}$ alkylsulfonyl, C$_{1-6}$ alkylsulfinyl, C$_{1-7}$ acyl, cyano, C$_{1-6}$ alkoxycarbonyl, C$_{1-7}$ acylamino, hydroxy, nitro, amino, aminocarbonyl, or aminosulfonyl, optionally N-substituted by one or two groups selected from C$_{1-6}$ alkyl, C$_{3-8}$ cycloalkyl, and C$_{3-8}$ cycloalkylC$_{1-4}$alkyl or disubstituted by C$_4$ or C$_5$ polymethylene; phenyl or phenyl C$_{1-4}$ alkyl group optionally substituted in the phenyl ring by one or two of halogen, C$_{1-6}$ alkoxy or C$_{1-6}$ alkyl groups, R$_2$ and R$_3$ are independently H or halogen;

In Group F, $R_1$ is H or $C_{1-6}$ alkyl, $R_2$ is H or halogen; and

In Group H, $R_{15}$ and $R_{16}$ are H or —CH=CH—CH=CH—;

X is NH or O; and

Z represents a radical of the formula

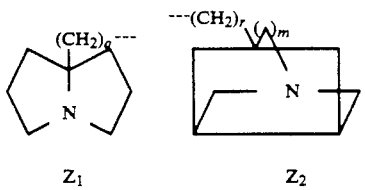

$Z_1$          $Z_2$ wherein m is 1 or 2, q is 1 or 2, and r is 0 or 1.

The term "cycloalkyl" embraces cyclic radicals having three to about ten ring carbon atoms, preferably three to about six carbon atoms, such as cyclopropyl and cyclobutyl. The terms "alkoxy" and "alkoxyalkyl" embrace linear or branched oxy-containing radicals each having alkyl portions of one to about ten carbon atoms, such as methoxy group.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl.

Included within the family of compounds of the described are the tautomeric forms of the described compounds, isomeric forms including diastereoisomers and individual enantiomers, and the pharmaceutically-acceptable salts thereof. The term "pharmaceutically-acceptable salts" embraces salts commonly used to form alkali metal salts and to form addition salts of free acids or free bases. Since the compounds contain basic nitrogen atoms, such salts are typically acid addition salts. The phrase "pharmaceutically-acceptable salts" is intended to embrace alkyl quaternary ammonium salts and n-oxides. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of the invention.

The compounds that are the subject of the invention herein can be prepared according to the following reaction schemes.

$Z_1$ is known and is prepared as described by Miyano and coworkers [J. Heterocyclic Chemistry (1987) 24, 47 for q=1; J. Pharmaceutical Sciences (1987), 76, 416 & references sited therein]. $Z_2$ is prepared according to schemes 1, 2, and 3.

Scheme 1 describes the preparation of amino-azacycles $Z_2$. The BOC-amine 1 (U.S. patent Application Ser. No. 07/515,391) is deprotected with trifluoroacetic acid and the resulting amine is cyclized intramolecularly with the exocyclic olefin by treatment with iodine and potassium iodide in the presence of sodium bicarbonate to yield the bridgehead iodide 2. Treatment of 2 with silver isocyanate affords the bridgehead isocyanate which may be hydrolyzed to give the requisite amine $Z_2$ wherein r=0. Alternatively treatment of 2 with silver cyanide affords the bridgehead nitrile which may be reduced to give the desired aminomethyl-azacycle $Z_2$ wherein r=1.

Scheme 2 illustrates the preparation of $Z_2$ hydroxy azacycles. Hydrolysis of bridgehead iodide 2 affords the desired hydroxy azacycle $Z_{2''}$ wherein r=0. Alternatively treatment of 2 with silver cyanade followed by hydrolysis and reduction gives the desired hydroxymethyl azacycle $Z_{2'''}$ wherein r=1.

Scheme 3 illustrates the preparation of ethano-bridged azatricycles ($Z_{2''''}$, wherein m=2). The azabicycloketone 3 is converted first to its O-benzyloxime. Removal of the N-BOC protecting group, followed by acylation with chloroacetic anhydride & iodide exchange, affords the intermediate 4. Cyclization under reductive radical-cyclization conditions (Bu:SnH, AIBN) affords the ethanobridged lactam 5. Reduction with lithium aluminum hydride affords the desired ethano-bridged azatricycle $Z_{2''''}$.

SCHEME 1
PREPARATION OF $Z_2$ AMINO-AZACYCLES

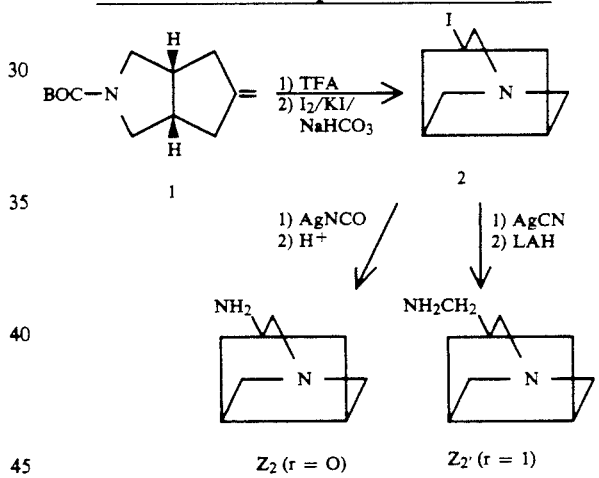

SCHEME 2
PREPARATION OF $Z_2$ HYDROXY AZACYCLES

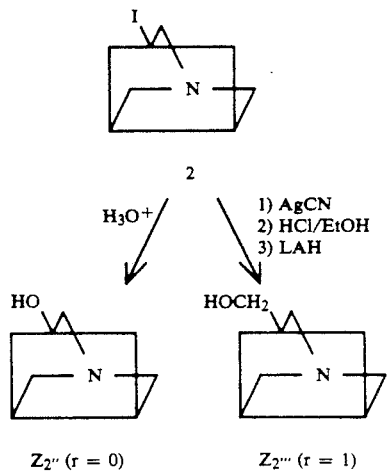

-continued
SCHEME 3
PREPARATION OF ETHANO-BRIDGED
MESO-AZATRICYCLE

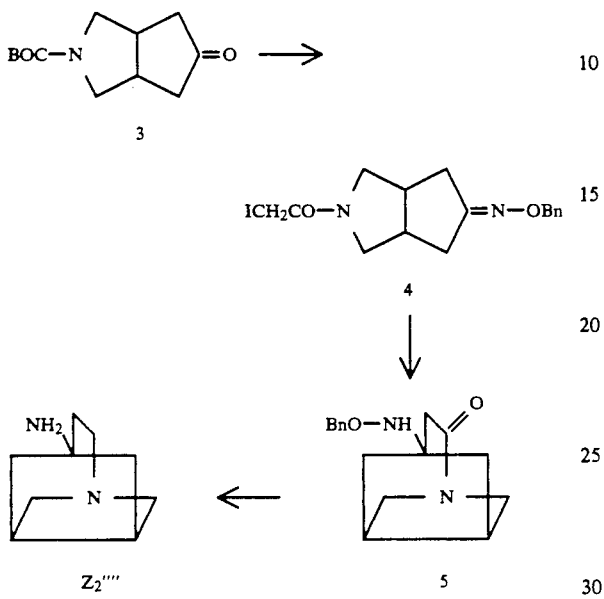

These examples, as well as all examples herein, are given by way of illustration only and are not to be construed as limiting the invention, either in spirit or scope, as many modifications, both in materials and methods, will be apparent from this disclosure to those skilled in the art. In these examples, temperatures are given in degrees Celsius (° C.) and quantities of materials in grams and milliliters unless otherwise noted.

EXPERIMENTALS

EXAMPLE A

Preparation of hexahydro-5-iodo-2,5β-methano-1H-3aα,6aα-cyclopenta [c]pyrrole

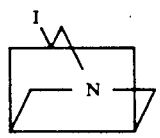

Cis-N-t-butoxycarbonylhexahydro-5-methylenecyclopenta[c]pyrrole [See Co-pending application Ser. No. 07/515,391 filed Apr.27, 1990] is treated with trifluoroacetic acid to afford an intermediate trifluoroacetate ammonium salt, which is then treated with base and I₂ to afford the title compound.

EXAMPLE B

Preparation of tetrahydro-2,5β-methano-1H-3aα,6aα-cyclopenta [c]pyrrol-5(3H)-amine

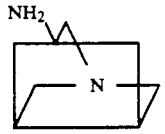

The iodo compound prepared in example A is treated with silver isocyanate to afford the intermediate N-formamide. This formamide is hydrolyzed to give the title compound.

EXAMPLE C

Preparation of tetrahydro-2,5β-methano-1H-3aα,6aα-cyclopenta [c]pyrrole-5(3H)-carbonitrile

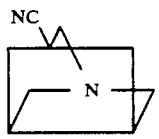

The iodo compound prepared in example A is treated with silver cyanide in dimethylformamide to afford the title compound.

EXAMPLE D

Preparation of tetrahydro-2,5β-methano-1H-3aα,6aα-cyclopenta [c]pyrrole-5(3H)-methanamine

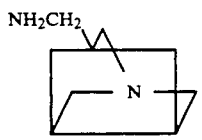

The nitrile compound prepared in example C is reduced with lithium aluminum hydride in etheral solvent to afford the title compound.

EXAMPLE E

Preparation of tetrahydro-2,5β-methano-1H-3aα, 6aαcyclopenta [c]pyrrole-5(3H)-methanol

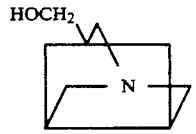

The nitrile compound prepared in example C is converted to the intermediate ethyl ester by treatment with aqueous ethanolic HCl. The ethyl ester is then treated with lithium aluminum hydride in etheral solvent to afford the title compound.

EXAMPLE F

Preparation of 1,1-dimethylethyl hexahydro-5-(phenylmethoxy)imino]cyclopenta[c]pyrrole-2(1H)-carboxylate

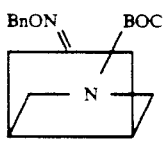

Cis-N-Butoxycarbonylhexahydro-5-oxo-cyclopenta[c]pyrrole is reacted with O-benzylhydroxylamine hydrochloride and sodium acetate in methanol to afford the title compound.

EXAMPLE G

Preparation of octahydro-2-(iodoacetyl)-5-[(phenylmethoxy)imino]cyclopenta[c]pyrrole

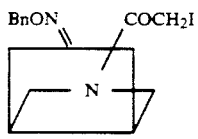

The title compound of example F is treated with trifluoroacetic acid in methylene chloride at room temperature. The volatiles are removed under reduced pressure to afford a residue which is treated with chloroacetic anhydride and triethylamine. The chloroacetylated material is then reacted with NaI in acetone to give the title compound.

EXAMPLE H

Preparation of hexahydro-5-[(phenylmethoxy)amino]-2,5β-ethano-1H-3aα, 6aα-cyclopenta[c]pyrrol-7-one

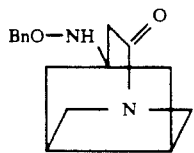

The title compound of example G is treated with tri-n-butylstannane in benzene at reflux containing a catalytic amount of AIBN. Upon workup the title compound is isolated.

EXAMPLE J

Preparation of tetrahydro-2,5β-ethano-1H-3aα, 6aα-cyclopenta [c]pyrrol-5(3H)-amine

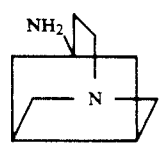

The title compound of example H is reacted with lithium aluminum hydride in tetrahydrofuran to afford after workup the title compound.

EXAMPLE 1

Preparation of 6-chloro-N-(tetrahydro-1H-pyrrolizin-7a(5H-ylmethyl-)imidazo [1,2-a]pyridine-8-carboxamide

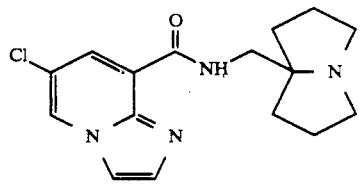

6-chloroimidazo[1,2-a]pyridine-8-carboxylic acid is reacted with carbonyldiimidazole in dimethylformamide and subsequently with 7a-aminomethylhexahydro-1H-pyrrolizine to afford the title compound upon workup.

EXAMPLE 2

Preparation of 6-chloro-N-(tetrahydro-2,5-β-methano-1H-3aα,6aα-cyclopenta [c]pyrrol-5(3H)-yl)imidazo[1,2-a]pyridine-8-carboxamide)

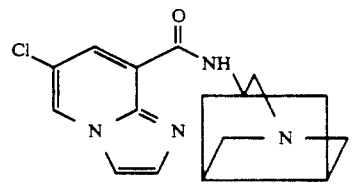

6-Chloroimidazo[1,2-a]pyridine-8-carboxylic acid is reacted with carbonyldiimidazole in dimethylformamide and subsequently with N-hexahydro-1H-2,5β-methano-3aα, 6aα-cyclopenta [c]pyrrol-5β-amine to afford the title compound upon workup.

EXAMPLE 3

Preparation of 3-ethyl-N-(tetrahydro-1H-pyrrolizin-7a(5H)-ylmethyl) indolizine-1-carboxamide

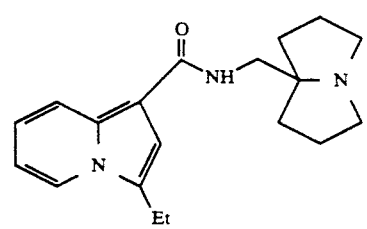

3-Ethylindolizine-1-carboxylic acid is reacted with carbonyldiimidazole in dimethylformamide and subsequently with 7a-aminomethylhexahydro-1H-pyrrolizine to afford the title compound upon workup.

EXAMPLE 4

Preparation of
3-ethyl-N-(tetrahydro-2,5β-methano-1H-3aα,6aα-cyclopenta
[c]pyrrol-5(3H)-yl)indolizine-1-carboxamide

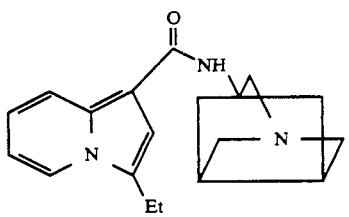

3-Ethylindolizine-1-carboxylic acid is reacted with carbonyldiimidazole in dimethylformamide and subsequently with N-hexahydro-1H-2,5β-methano-3aα, 6aα-cyclopenta [c]pyrrol-5α-amine to afford the title compound upon workup.

EXAMPLE 5

Preparation of
3-ethyl-N-(tetrahydro-1H-pyrrolizin-7a(5H)-ylmethyl)imidazo [1,2-a]pyridine-1-carboxamide

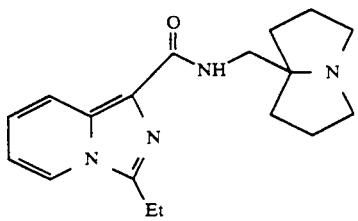

3-Ethylimidazo[1,5-a]pyridine-1-carboxylic acid is reacted with carbonyldiimidazole in dimethylformamide and subsequently with 7a-aminomethylhexahydro-1H-pyrrolizine to afford the title compound upon workup.

EXAMPLE 6

Preparation of
3-ethyl-N-(tetrahydro-2,5β-methano-1H-3aα,6aα-cyclopenta
[c]pyrrol-5(3H)-yl)imidazo[1,5a]pyridine-1-carboxamide

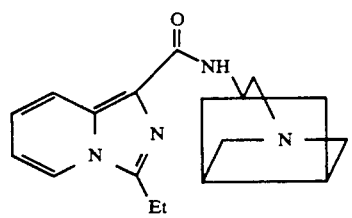

3-Ethylimidazo[l,5-a]pyridine-I-carboxylic acid is reacted with carbonyldiimidazole in dimethylformamide and subsequently with N-hexahydro-1H-2,5β-methano-3aα, 6aα-cyclopenta [c]pyrrol-5α-amine to afford the title compound upon workup.

EXAMPLE 7

Preparation of
N-(tetrahydro-1H-pyrrolizin-7a(5H)-ylmethyl)imidazo [1,2-a]pyridine-2-carboxamide

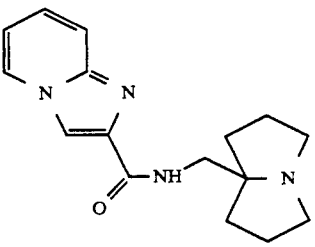

Imidazo[1,2-a]pyridine-2-carboxylic acid is reacted with carbonyldiimidazole in dimethylformamide and subsequently with 7a-aminomethylhexahydro-1H-pyrrolizine to afford the title compound upon workup.

EXAMPLE 8

Preparation of
N-(tetrahydro-2,5β-methano-1H-3aα,6aα-cyclopenta [c]pyrrol-5(3H)-yl)imidazo[1,2-a]pyridine-2-carboxamide

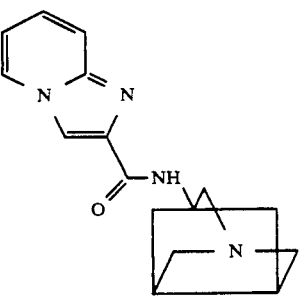

Imidazo[1,2-a]pyridine-2-carboxylic acid is reacted with carbonyldiimidazole in dimethylformamide and subsequently with N-hexahydro-1H-2,5β-methano-3aα,6aα-cyclopenta [c]pyrrol-5α-amine to afford the title compound upon workup.

The compounds of examples 1-8 find utility as antagonists of the serotonin 5-HT$_3$ receptor. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbencies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

The compounds herein exhibit 5-HT$_3$ antagonism. 5-HT$_3$ antagonism can be determined by the radioligand receptor binding assay as described herein and in the in vivo Bezold-Jarisch reflex procedure.

Serotonin (5-HT$_3$)

Procedure

GR65630 binds to the 5-HT$_3$ receptor. Brain cortices are obtained from male rats and a membrane fraction prepared by standard techniques. 0.04 mg of membrane prep is incubated with 0.2 nM [$^3$H]-GR656630 for 60 minutes at 22° C. Non-specific binding is estimated in the presence of 1 uM ICS 205-930. Membranes are filtered and washed 3 times and the filters are counted to determine [3H]-GR65630 specifically bound.*

*Literature References: Kilpatrick GJ, Jones BJ and Tyers MG. Identification and distribution of 5-HT$_3$ receptors in rat brain using radioligand binding. Nature, 330 : 746-748, 1987.

Results

Kd = 2.46 nM
Bmax = 154 fmol/mg protein
% Specific Binding: 70

| Effect of Reference Compounds on [H]-GR65630 Bound (0.2 nM) | | | |
|---|---|---|---|
| Compound | IC$_{50}$ | Ki | Hill Coefficient |
| Quipazine | 0.5 nM | 0.18 nM | 0.86 |
| ICS 205-930 | 2.2 nM | 0.51 nM | 1.0 |
| 5-HT | 122 nM | 0.39 uM | 1.0 |
| RU24969 | 320 nM | 1.85 uM | 1.0 |
| Zacopride | 0.55 nM | 0.18 nM | 0.86 |

Bezold-Jarisch Reflex

The test sample is administered i.p. (mg/kg) to a group of 3 mice. Thirty minutes later, a 5-HT (0.25 mg/kg i.v.)-induced bradycardia is recorded in pentobarbital anesthetized animals. A greater than 50 percent (>50) reduction in the bradycardic response relative to vehicle-treated control mice is considered significant.

| REFERENCE AGENTS: | Minimum Effective Dose (MED), mg/kg |
|---|---|
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methysergide | >10 |
| metoclopramide | 5 |
| scopolamine | 2.5 |

This method has been described by Saxena, P. R. and Lawang, A., Arch. Int. pharmaCodyn., 277:235-252, 1985.

Also embraced within this invention is a class of pharmaceutical compositions comprising one or more of the described compounds in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intrapertoineally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

For therapeutic purposes, the compounds of this invention are ordinarily combined with one or more adjuvants appropriate to the indicated route of administration. If administered cer os, the compounds may be admixed with lactose, sucrose, starch powder, cellulose esters of alkanoic acids, cellulose alkyl esters, talc, stearic acid, magnesium stearate, magnesium oxide, sodium and acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

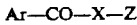

the stereoisomers and pharmaceutically acceptable salts thereof, wherein Ar represents a radical of the formula:

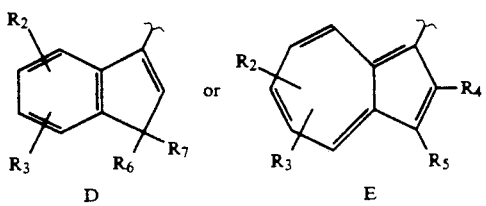

wherein in Group D, one of R$_6$ or R$_7$ is C$_{1-6}$ alkyl and the other is C$_{1-6}$ alkyl, phenyl or phenyl C$_{1-4}$ alkyl optionally substituted in either phenyl ring by one or two of $C_{1-6}$ alkyl, $C_{1-6}$ alkoxy, or halogen, or $R_6$ and $R_7$ together are $C_{2-6}$ polymethylene or $C_{2-5}$ polymethylene interrupted by an —O— linkage, $R_2$ and $R_3$ are independently H or halogen;

wherein in Group E, $R_4$ is H or $C_{1-6}$ alkoxy, $R_5$ is H or $C_{1-6}$ alkoxy, $R_2$ is H, halogen, $CF_3$, $C_{1-6}$ alkyl, $C_{1-6}$ alkoxy, $C_{1-6}$-alkylthio, $C_{1-6}$ alkylsulfonyl, $C_{1-6}$ alkylsulfinyl, $C_{1-7}$ acyl, cyano, $C_{1-6}$ alkoxycarbony, $C_{1-7}$ acylamino, hydroxy, nitro, amino, aminocarbonyl, or aminosulfonyl, optionally N-substituted by one or two groups selected from $C_{1-6}$ alkyl, $C_{3-8}$ cycloalkyl, $C_{3-8}$ cycloalkyl and $C_{1-4}$alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups, $R_2$ and $R_3$ are independently H or halogen;

X is NH or O; and

Z represents a radical of the formula

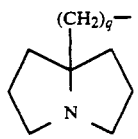

wherein q is 1 or 2.

2. A compound according to claim 1 wherein Ar is group D.

3. A compound according to claim 1 wherein Ar is group E.

4. A pharmaceutical composition for the treatment of anxiety, psychoses, depression, gastrointestinal motility disturbances or conditions responsive to 5-$HT_3$ antagonist effect comprising a therapeutically effective amount of a compound as defined in claim 1 and a pharmaceutically acceptable carrier or diluent.

5. A pharmaceutical composition according to claim 4 wherein Ar is group D.

6. A pharmaceutical composition according to claim 4 wherein Ar is Group E.

* * * * *

UNITED STATES PATENT AND TRADEMARK OFFICE
CERTIFICATE OF CORRECTION

PATENT NO. : 5,196,547    Page 1 of 3

DATED : March 23, 1993

INVENTOR(S) : Flynn, et al.

It is certified that error appears in the above-identified patent and that said Letters Patent is hereby corrected as shown below:

Cover page, left-hand column, line 4, reading "Inventors: Daniel P. Becker, Glenview; Daniel L. Flynn, Mundelein; Alan E. Moormann, Skokie; Roger Nosal, Buffalo Grove; Clara I. Villamil, Glenview, all of Ill." should read -- Inventors: Daniel L. Flynn, Mundelein; Alan E. Moormann, Skokie, both of Ill. --.

Column 2, line 23, reading "anti-arraythmic" should read -- anti-arrythmic --.

Column 2, line 36, reading "4-NMe$_2$3-" should read -- 4-NMe$_2$, 3- --.

Column 2, line 40, reading "alkoxycarbonylamini," should read -- alkoxycarbonylamino, --.

Column 2, line 41, reading "athoxy" should read -- ethoxy --.

Column 2, line 55, reading "pair of" should read -- pair or --.

Column 4, line 23, reading "A, R is H," should read -- A, R$_1$ is H, --.

Column 4, line 55, reading "-)- linkage, linkage," should read -- -O- linkage, --.

Column 6, line 22, reading "(Bu:SnH," should read -- (Bu$_3$SnH, --.

Column 8, line 55, reading "6aαcyclopenta" should read -- 6aα-cyclopenta --.

UNITED STATES PATENT AND TRADEMARK OFFICE
CERTIFICATE OF CORRECTION

PATENT NO. : 5,196,547
DATED : March 23, 1993
INVENTOR(S) : Flynn, et al.

It is certified that error appears in the above-identified patent and that said Letters Patent is hereby corrected as shown below:

Column 9, line 4, reading "5-(phenylmethoxy)" should read -- 5-[(phenylmethoxy) --.

Column 10, line 27, reading "2,5-β-" should read -- 2,5β- --.

Column 11, line 64, reading "-I-carboxylic" should read -- 1-carboxylic --.

Column 13, line 12, reading "Tyers MG." should read -- Tyers MB.

Column 13, line 52, reading "pharmaCodyn.," should read -- Pharmacodyn., --.

Column 14, line 1, reading "intrapertoineally" should read -- intraperitoneally --.

Column 14, line 19, reading "cer os," should read -- per os, --.

Column 14, line 23, reading "and acacia" should read -- and calcium salts of phosphoric and sulfuric acids, gelatin, acacia --

UNITED STATES PATENT AND TRADEMARK OFFICE
CERTIFICATE OF CORRECTION

PATENT NO. : 5,196,547
DATED : March 23, 1993
INVENTOR(S) : Flynn, et al

It is certified that error appears in the above-indentified patent and that said Letters Patent is hereby corrected as shown below:

Column 15, line 10, reading "alkoxycarbony," should read --alkoxycarbonyl, --.

Signed and Sealed this

Fourteenth Day of June, 1994

Attest:

BRUCE LEHMAN

*Attesting Officer*  *Commissioner of Patents and Trademarks*